United States Patent [19]
Castelli

[11] Patent Number: 5,928,141
[45] Date of Patent: Jul. 27, 1999

[54] ELECTRODE FOR DETECTING AN ELECTRIC BIOLOGICAL SIGNAL, IN PARTICULAR AN ELECTROCARDIOGRAPHIC SIGNAL

[76] Inventor: Arrigo Castelli, 6900 Lugano, Via Gerso 3, Switzerland

[21] Appl. No.: 08/688,958

[22] Filed: Jul. 31, 1996

[30] Foreign Application Priority Data

Aug. 1, 1995 [IT] Italy ................................. TO95A0645

[51] Int. Cl.⁶ ....................................................... A61B 5/04
[52] U.S. Cl. ........................... 600/372; 600/396; 600/509
[58] Field of Search .................................. 128/639–644, 128/690, 696, 635; 607/152, 153; 600/396, 397, 395, 391, 392, 509

[56] References Cited

U.S. PATENT DOCUMENTS

| | | | |
|---|---|---|---|
| 2,887,112 | 5/1959 | Smith | 600/395 |
| 3,340,868 | 9/1967 | Darling | 600/392 |
| 3,487,827 | 1/1970 | Edmark | 128/641 |
| 3,746,004 | 7/1973 | Jankelson | 607/153 |
| 4,166,453 | 9/1979 | McClelland | 128/639 |
| 4,311,151 | 1/1982 | Hagihara | 128/635 |
| 4,375,219 | 3/1983 | Schmid | 128/639 |
| 4,383,529 | 5/1983 | Webster | 607/153 |
| 4,535,783 | 8/1985 | Marangoni | 128/639 |
| 4,809,705 | 3/1989 | Ascher | 128/639 |

FOREIGN PATENT DOCUMENTS

| | | | |
|---|---|---|---|
| 2 581 855 | 2/1985 | France | A61B 5/04 |
| 3040098 | 6/1982 | Germany | 128/696 |
| WO 80/01538 | 8/1980 | WIPO | A61B 10/00 |

*Primary Examiner*—Danton D. DeMille
*Assistant Examiner*—David M Ruddy
*Attorney, Agent, or Firm*—Darby & Darby

[57] ABSTRACT

An electrode for detecting an electric biological signal, in particular an electrocardiographic signal, and presenting a metal conducting disk and a rigid net of constant thickness and superimposed on the metal disk. A small amount of conducting fluid is poured on to and spreads throughout the net to form a layer of conducting fluid superimposed on the metal disk and presenting a constant thickness.

21 Claims, 1 Drawing Sheet

ELECTRODE FOR DETECTING AN ELECTRIC BIOLOGICAL SIGNAL, IN PARTICULAR AN ELECTROCARDIOGRAPHIC SIGNAL

BACKGROUND OF THE INVENTION

The present invention relates to an electrode for detecting an electric biological signal, in particular an electrocardiographic signal.

Currently known instruments for detecting electrocardiographic signals present at least two external electrodes, which are applied to portions of the human body (e.g. one on the left and one on the right arm) for detecting electric biological body signals generated by the action of the heart.

The electrodes are substantially flat, and are normally applied to the body by means of straps or adhesive means on the electrode itself; and, to improve electrical contact between the electrode and the body, a thin layer of conducting gel is normally applied between the two. The layer of conducting gel, however, which is not applied evenly over the electrode and therefore varies in thickness, fails to provide for an optimum distance between the electrode and the body. In particular, on certain parts of the electrode, the thickness of the gel may be such as to present a contact resistance unsuited to the characteristics of the electrocardiographic signal detecting instrument.

Moreover, the above means of securing the electrodes fail to provide for rigidly connecting the electrically contacting parts, and permit relative movements resulting in noise in the electric signal, even to the extent of impairing the outcome of the electrocardiogram.

SUMMARY OF THE INVENTION

It is an object of the present invention to provide an electrode for detecting an electric biological signal, in particular an electrocardiographic signal, designed to overcome the above drawbacks typically associated with known electrodes.

According to the present invention, there is provided an electrode for detecting an electric biological signal, in particular an electrocardiographic signal, as claimed in claim 1.

BRIEF DESCRIPTION OF THE DRAWINGS

A preferred, non-limiting embodiment of the present invention will be described by way of example with reference to the accompanying drawings, in which.

DETAILED DESCRIPTION OF THE INVENTION

Figure 1:
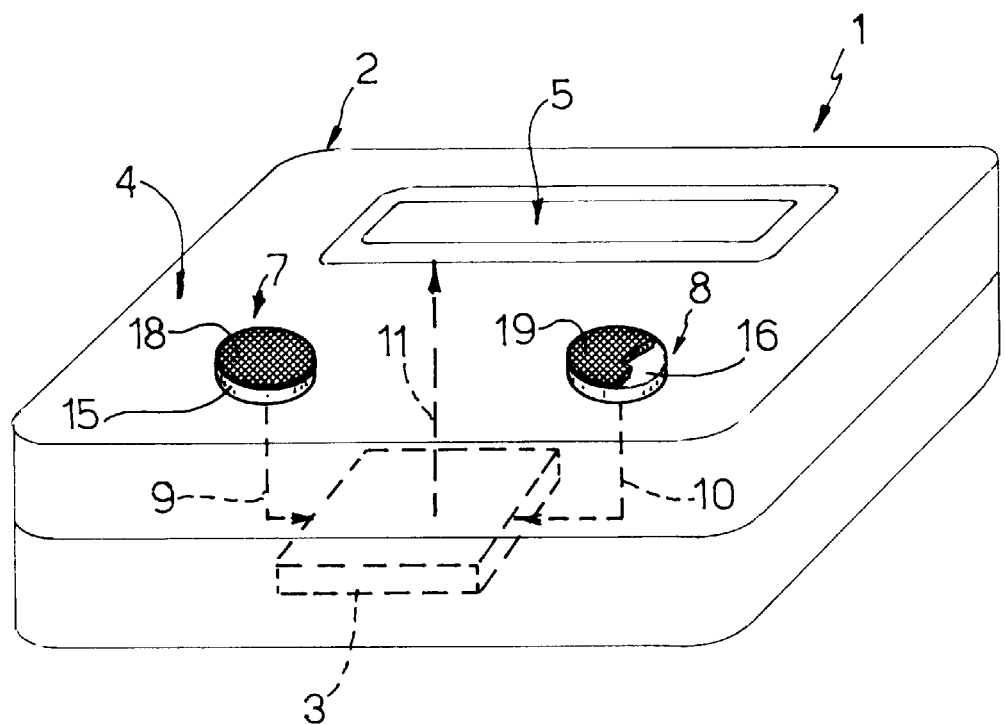
FIG. 1 shows a view in perspective of an instrument for detecting an electric biological signal, in particular an electrocardiographic signal, featuring electrodes in accordance with the teachings of the present invention.

Number 1 in FIG. 1 indicates a pocket instrument for detecting an electrocardiographic signal, and comprising a substantially parallelepiped outer casing 2, and a known electronic processing circuit 3 (shown schematically) housed inside casing 2.

More specifically, casing 2 presents a flat rectangular wall 4 fitted with a display 5 and two input signal detecting electrodes 7, 8.

Circuit 3 is supplied with and processes an electrocardiographic electric signal, and itself supplies various information, shown on display 5, relative to cardiac activity (e.g. the number of beats per minute, electrocardiographic trace, etc.).

Electrodes 7, 8 communicate with circuit 3 over respective electric wires 9, 10, and circuit 3 communicates with display 5 over an electric line (bus) 11.

Figure 2:
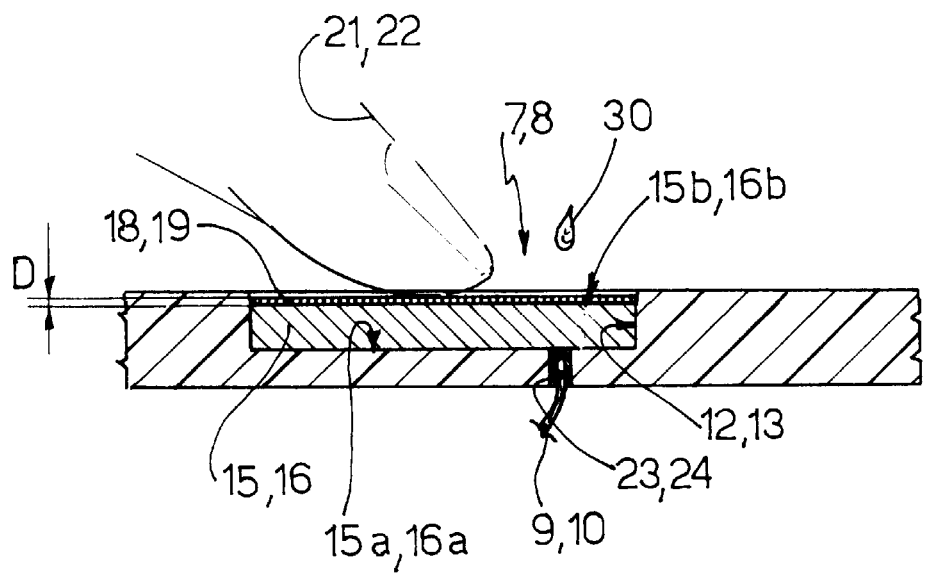
FIG. 2 shows a cross section of an electrode in accordance with the present invention.

Wall 4 presents two cylindrical dead holes 12, 13, each housing a respective electrode 7, 8; and each electrode 7, 8 according to the present invention (FIG. 2) comprises a circular conducting disk 15, 16 housed inside hole 12, 13, and a rigid net 18, 19 superimposed on disk 15, 16.

Each conducting disk 15, 16 presents a first circular face 15a, 16a contacting the bottom of cylindrical dead hole 12, 13, and a second face 15b, 16b to which net 18, 19 is applied; and net 18, 19 is circular in shape, presents a constant thickness D, is made of synthetic insulating material, e.g. Nylon, and is fixed stably, e.g. by means of adhesive, to conducting disk 15, 16, which is made of metal material, in particular chloridized silver.

The bottom of each cylindrical dead hole 12, 13 presents a through hole 23, 24 engaged by electric wire 9, 10 extending from first face 15a, 16a to electronic circuit 3.

In actual use, a small amount of conducting fluid 30, in particular chlorinated water, is poured on to and spreads evenly throughout net 18, 19 to form a layer of fluid of constant thickness D retained by net 18, 19 and superimposed on conducting disk 15, 16.

The user (not shown) of instrument 1 then places two parts 21, 22 of the body on respective electrodes 7, 8. More specifically, the user (not shown) grips outer casing 2, places the right and left thumb 21, 22 on respective electrodes 7, 8, and with the ball of the thumb presses on nets 18, 19.

The layer of conducting fluid 30 thus provides for ohmic contact between portions 21, 22 and respective conducting disks 15, 16 to connect portions 21, 22 to electric wires 9, 10 and transfer the biological body signal to circuit 3. Since net 18, 19 is in no way deformed by the pressure applied by the user, the thickness D of the layer of conducting fluid remains constant.

The advantages of the present invention will be clear from the foregoing description. In particular, electrode 7, 8 provides for ohmic connection of a conductor (disk 15, 16) and a portion of the body (portion 21, 22) via a conducting means (conducting fluid) performing the same function as the gel used on known electrodes, but which presents a constant thickness regardless of the position of the body portion on the electrode.

Moreover, net 18, 19 presents a thickness D corresponding to the optimum distance between the body portion and the conductor; and, even in the event of the body portion moving in relation to the electrode, the thickness of the conducting means remains unchanged, so that no noise is produced in the detected electric signal.

Clearly, changes may be made to the electrode as described and illustrated herein without, however, departing from the scope of the present invention. For example, as opposed to chlorinated water, any other liquid solution with similar conducting characteristics may be used for achieving ohmic contact as described above.

I claim:

1. An electrode for detecting an electric biological signal, said electrode comprising:

a substantially flat conducting means having a predetermined surface area; and a substantially flat and substantially rigid net having a contact surface no larger than said predetermined surface area and superimposed on said conducting means, said net presenting a substantially constant thickness;

said net receiving a conducting fluid, which spreads evenly through the net to form a layer of conducting fluid superimposed on said conducting means, retained by said net, such that said substantially rigid net maintains said substantially constant thickness when subjected to pressure supplied by a user.

2. An electrode as claimed in claim 1, wherein said conducting means comprise at least one flat conductor;

said net being located contacting a first face of said flat conductor.

3. An electrode as claimed in claim 2, and including connecting means for connecting said conducting means to a processing means;

said connecting means communicating with a second face of said flat conductor.

4. An electrode as claimed in claim 2, wherein said net is fixed by an adhesive material to said first face of said flat conductor.

5. An electrode as claimed in claim 1, wherein said net is made of insulating material.

6. An electrode as claimed in claim 1, wherein said net comprises an indeformable-mesh net superimposed on said conducting means.

7. An electrode as claimed in claim 1, wherein said conducting means comprise at least a metal portion made of chloridized silver.

8. An electrode for detecting an electric biological signal from a body member, said electrode comprising:

a substantially flat conductor having a predetermined surface area; and a substantially flat and substantially rigid net having a contact surface no larger than said predetermined surface area and superimposed on said conductor and presenting a substantially constant thickness, said net receiving a conducting fluid, which spreads evenly through the net to form a layer of conducting fluid superimposed on said conductor and, as said body member contacts said substantially rigid net to apply pressure thereto, maintain said substantially constant thickness.

9. An electrode as claimed in claim 8, wherein said conductor comprises at least one flat conductor; and said net being located contacting a first face of said flat conductor.

10. An electrode as claimed in claim 9, further including a connector for connecting said conductor to a processor; said connector communicating with a second face of said flat conductor.

11. An electrode as claimed in claim 9, wherein said net is fixed by an adhesive material to said first face of said flat conductor.

12. An electrode as claimed in claim 8, wherein said net is made of an insulating material.

13. An electrode as claimed in claim 8, wherein said net comprises an indeformable-mesh superimposed on said conductor.

14. An electrode as claimed in claim 8, wherein said conductor comprises at least a metal portion made of chloridized silver.

15. An electrode for detecting an electric biological signal, said electrode comprising:

a substantially flat conductor; and a substantially flat and substantially rigid net superimposed on said conductor and presenting a substantially constant thickness, said net including a plurality of mesh elements that create pores sufficient to retain a conducting liquid, said net receiving said conducting liquid which spreads evenly through said net to form a layer of conducting fluid superimposed on said conductor and, as a body member contacts said substantially rigid net to apply pressure thereto, maintain said substantially constant thickness.

16. An electrode according to claim 15 wherein:

said conductor comprises at least one flat conductor having respective first and second faces; and said net being located contacting said first face of said flat conductor.

17. An electrode according to claim 16 and further including:

a processor; and a connector for connecting said conductor to said processor, said connector communicating with said second face of said flat conductor.

18. An electrode according to claim 16 wherein:

said net is fixed by an adhesive material to said first face of said flat conductor.

19. An electrode according to claim 15 wherein:

said net is made of an insulating material.

20. An electrode according to claim 15 wherein:

said net comprises an indeformable-mesh superimposed on said conductor.

21. An electrode according to claim 15 wherein:

said conductor comprises at least a metal portion made of chloridized silver.

* * * * *